US009841321B2

(12) United States Patent
Pastore et al.

(10) Patent No.: US 9,841,321 B2
(45) Date of Patent: Dec. 12, 2017

(54) VISUAL INDICATOR OF SCAN WORKFLOW

(71) Applicant: Thermo Scientific Portable Analytical Instruments Inc., Tewksbury, MA (US)

(72) Inventors: Timothy M. Pastore, Wakefield, MA (US); David Perez, Milford, MA (US); Michael D. Hargreaves, Lawrence, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 0 days.

(21) Appl. No.: 15/406,968

(22) Filed: Jan. 16, 2017

(65) Prior Publication Data

US 2017/0299431 A1    Oct. 19, 2017

Related U.S. Application Data

(63) Continuation of application No. 14/573,594, filed on Dec. 17, 2014.

(Continued)

(51) Int. Cl.
*G01J 3/12* (2006.01)
*G01J 3/02* (2006.01)
(Continued)

(52) U.S. Cl.
CPC ............ *G01J 3/0264* (2013.01); *G01J 3/027* (2013.01); *G01J 3/0272* (2013.01); *G01J 3/10* (2013.01); *G01J 3/28* (2013.01); *G01J 3/2803* (2013.01); *G01J 3/42* (2013.01); *G01J 3/44* (2013.01); *G01N 21/552* (2013.01); *G01N 21/359* (2013.01); *G01N 21/65* (2013.01); *G01N 21/718* (2013.01); *G01N 2021/3595* (2013.01);
(Continued)

(58) Field of Classification Search
CPC .... G01J 3/02; G01J 3/28; G01J 3/2803; G01J 3/10; G01J 3/2823
USPC ......................................................... 356/326
See application file for complete search history.

(56) References Cited

U.S. PATENT DOCUMENTS 7,381,972 B1    6/2008   Varmette et al.
7,928,391 B2    4/2011   Azimi et al.
(Continued)

FOREIGN PATENT DOCUMENTS

DE    202012006556    12/2012

*Primary Examiner* — Tarifur Chowdhury
*Assistant Examiner* — Md M Rahman
(74) *Attorney, Agent, or Firm* — William R. McCarthy, III

(57) ABSTRACT

A hand-held spectrometer includes at least one indicator light and a processor configured to control the at least one indicator light to indicate a state of the hand-held spectrometer selected from a group consisting of a background scanning state, a ready-to-scan-sample state, a signal strength state, a fluorescence intensity state, a sample match state, a sample classification state, an error state, a data transfer state, a battery charge state, and a memory capacity state. The sample match state can be, for example, one of a positive match state, a mixture match state, a negative match state, and a match error state. In some embodiments, the error state can be at least one of a background error state, a user error state, and an instrument error state, or any combination thereof.

18 Claims, 4 Drawing Sheets

Related U.S. Application Data

(60) Provisional application No. 61/918,635, filed on Dec. 19, 2013.

(51) Int. Cl.
*G01J 3/42* (2006.01)
*G01J 3/44* (2006.01)
*G01N 21/552* (2014.01)
*G01J 3/28* (2006.01)
*G01J 3/10* (2006.01)
*G01N 21/65* (2006.01)
*G01N 21/71* (2006.01)
*G01N 21/35* (2014.01)
*G01N 21/39* (2006.01)
*G01N 21/359* (2014.01)

(52) U.S. Cl.
CPC ............... *G01N 2021/399* (2013.01); *G01N 2201/0221* (2013.01)

(56) References Cited

U.S. PATENT DOCUMENTS

| | | | |
|---|---|---|---|
| 8,699,020 B1 * | 4/2014 | Zhou | G01J 3/0264 356/301 |
| 2005/0229698 A1 | 10/2005 | Beecroft et al. | |
| 2005/0248758 A1 | 11/2005 | Carron et al. | |
| 2006/0284094 A1 | 12/2006 | Inbar | |
| 2007/0194239 A1 | 8/2007 | McAllister et al. | |
| 2008/0191137 A1 | 8/2008 | Poteet et al. | |
| 2008/0291426 A1 | 11/2008 | Azimi et al. | |
| 2008/0319286 A1 | 12/2008 | Ridder et al. | |
| 2009/0257046 A1 | 10/2009 | Dean et al. | |
| 2009/0321648 A1 | 12/2009 | Shelley et al. | |
| 2010/0296285 A1 * | 11/2010 | Chemel | F21S 2/005 362/235 |
| 2010/0315629 A1 * | 12/2010 | Knopp | G01J 3/02 356/301 |
| 2011/0309247 A1 * | 12/2011 | Azimi | G01J 3/02 250/339.01 |
| 2013/0016337 A1 | 1/2013 | Gardner et al. | |
| 2014/0176940 A1 | 6/2014 | Fishbine et al. | |
| 2014/0374601 A1 | 12/2014 | Pastore et al. | |

\* cited by examiner

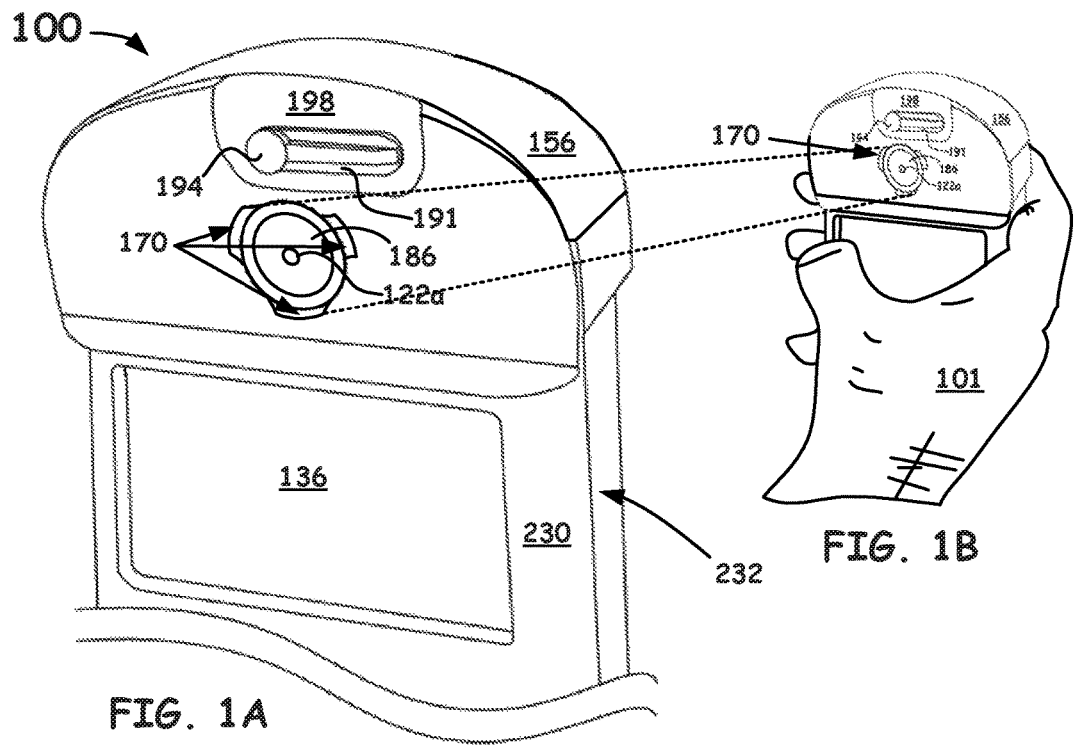
FIG. 1A
FIG. 1B
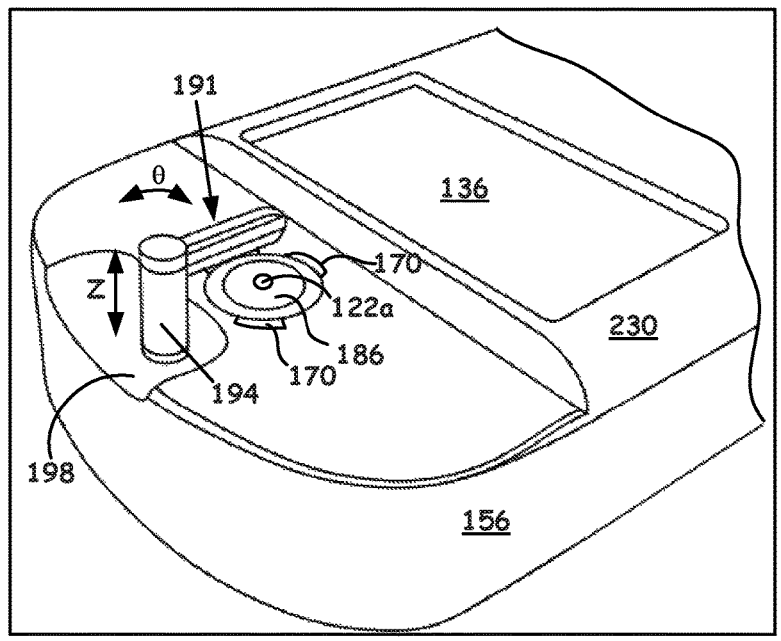
FIG. 1C

VISUAL INDICATOR OF SCAN WORKFLOW

CLAIM OF PRIORITY

This application is a continuation of and claims priority from U.S. patent application Ser. No. 14/573,594, filed Dec. 17, 2014, which claims the benefit of U.S. provisional patent application No. 61/918,635, filed Dec. 19, 2013. The contents of these applications are incorporated by reference in their entireties.

GOVERNMENT SUPPORT

This invention was made with Government support under Contract Number N00178-04-D-4143 awarded by Naval Explosive Ordinance Disposal Technology Division (NAVEODTECHDIV). The Government has certain rights in the invention.

FIELD OF THE INVENTION

The present invention relates to spectroscopy and more specifically, the present invention relates to a visual indicator system and method for hand-held spectrometers, such as FTIR and/or Raman hand-held spectrometers, that can also automatically, using visual indicators, provide information to the user, for example under less-than-ideal conditions.

BACKGROUND

Attenuated total reflectance (ATR) is an optical interrogation technique often used in conjunction with infrared spectroscopy (e.g., Fourier Transform Infrared (FTIR)), which enables samples to be examined directly in a solid or liquid state.

In particular, ATR capitalizes on total internal reflected light produced at the interface of a configured internally reflecting element (IRE) and a coupled sample plane. In operation, a beam of light (e.g., infrared) is passed through the IRE crystal in such a way that it reflects at least once off of the internal surface in contact with the sample. This reflection forms an evanescent wave which extends into the sample, often up to about 5 microns, with the exact value being determined by the wavelength of light, the angle of incidence and the indices of refraction for the IRE crystal and the sample medium being interrogated. The reflected beam, which carries the spectral information of the sample, is thereafter interrogated for analysis via, for example, a single pixel, linear array or 2 dimensional array detector.

Raman spectroscopy is an optical interrogation, which enables samples to be examined directly in solid, liquid or gas state.

Raman, has the advantage, in backscatter collection mode that it can collect data through transparent containers, such as vials, bottles and plastic bags. In operation, a beam of monochromatic laser light is directed at and into the sample. This induces the molecules in the sample to vibrate, consuming some of the laser energy. Light is rescattered from the sample, and the rescattered light contains spectral information that is unique to the sample. This is thereafter interrogated for analysis, via, for example a charge-coupled-detector (CCD), linear or 2-dimensional array detectors or a InGaAs linear array or 2 dimensional array detector.

The workflow of handheld FTIR and/or Raman spectrometers requires an operator to perform specific steps in order to have the instrument perform correctly. One of the most common issues with the FTIR workflow using ATR/FTIR hand-held spectrometers is that a first responder donned in, for example, a hazmat suit, has difficulty in following the workflow to successfully execute a scan of a desired sample, primarily because of limited visibility and dexterity. The issue of visibility is exacerbated by the fact that the user is not able to read instructions on the screen, because the mask of the suit often can be fogged as a result of the user operating in the field.

Accordingly, a need exists for a means to allow a first responder operator of hand-held spectrometers to obtain scans of samples in hazardous conditions without having to read specific operating instructions. The present invention is directed to this need by providing a compact hand-held spectrometer that is configured to provide visual indicators close to the sensing area so that the user can operate the device without reading the screen.

SUMMARY

The invention is generally directed to providing an indication close to the sensing area of a hand-held spectrometer to direct a user as to what to do without the user having to read the screen.

In one embodiment, a hand-held spectrometer includes at least one indicator light and a processor configured to control the at least one indicator light to indicate a state of the hand-held spectrometer selected from a group consisting of a background scanning state, a ready-to-scan-sample state, a signal strength state, a fluorescence intensity state, a sample match state, a sample classification state, an error state, a data transfer state, a battery charge state, and a memory capacity state. The sample match state can be, for example, one of a positive match state, a mixture match state, a negative match state, and a match error state. The sample classification state can be an explosive (e.g., triacetone triperoxide (TATP), RDX, hexamethylene triperoxidediamine (HMTD)) match state, a narcotic (e.g., heroin, cocaine, methamphetamine, JWH-18) match state, a biological material (e.g., anthrax, botulism) match state, and a toxic material (e.g., acrolein, chlorosulfonic acid, isopropyl isocyanate, toluene, 2,4-diisocyanate) match state, or any combination thereof. In some embodiments, the error state can be at least one of a background error state, a user error state, and an instrument error state, or any combination thereof. In certain embodiments, the hand-held spectrometer can further include an attenuated total reflection (ATR) platform, and at least one indicator light can be adjacent to the ATR platform. In some embodiments, at least one indicator light can be located around the ATR platform.

In another embodiment, a method of using a hand-held spectrometer includes providing at least one indicator light configured to indicate a state of the hand-held spectrometer, and activating a scan function of the hand-held spectrometer, thereby changing the state of the hand-held spectrometer and the at least one indicator light to indicate a background scanning state while acquiring a background scan, and, after completion of the background scan, either a ready-to-scan-sample state or an error state. The method also includes thereafter acquiring a sample spectrum, and displaying the sample spectrum. Changing the state of the hand-held spectrometer and the at least one indicator light to an error state can include changing the state of the at least one indicator light to indicate at least one of a background error state, a user error state, and an instrument error state, or any combination thereof. In some embodiments, the method can further include, after acquiring the sample spectrum, matching the sample to a spectrum library and changing the state of the at least one indicator light to indicate a sample match state. The sample match state can be one of a positive match state, a mixture match state, a negative match state, and a match error state. In certain embodiments, the method can further include transferring sample spectrum data and changing the state of the at least one indicator light to indicate a data transfer state. In some embodiments, the method can further include charging a battery of the handheld spectrometer and changing the state of the at least one indicator light to indicate a battery charge state. In certain embodiments, the method can further include, after acquiring the sample spectrum, storing the sample spectrum, and changing the state of the at least one indicator light to indicate a memory capacity state. In some embodiments, the method can further include changing the state of the at least one indicator light to indicate a signal strength state. In certain embodiments, the method can further include changing the state of the at least one indicator light to indicate a fluorescence intensity state.

This invention has many advantages, such as enabling a user to receive spectrometer operating instructions without the user having to read the screen. This capability is beneficial over current methods because the masks that the first responders use typically fog due to the condensation of perspiration. This makes reading the screen difficult. In particular, single colors are much easier to see than text on a screen.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1A shows an example isometric cutaway perspective of an ATR handheld instrument with three indicator lights to aid an operator in the field.

FIG. 1B illustrates the hand-held form factor of the instrument in gloved operation.

FIG. 1C also shows an example isometric cutaway perspective of an ATR handheld instrument but not in operation with three indicator lights (the third indicator light 170 is obscured by the anvil arm 191) to aid an operator in the field.

DETAILED DESCRIPTION

Figure 2:
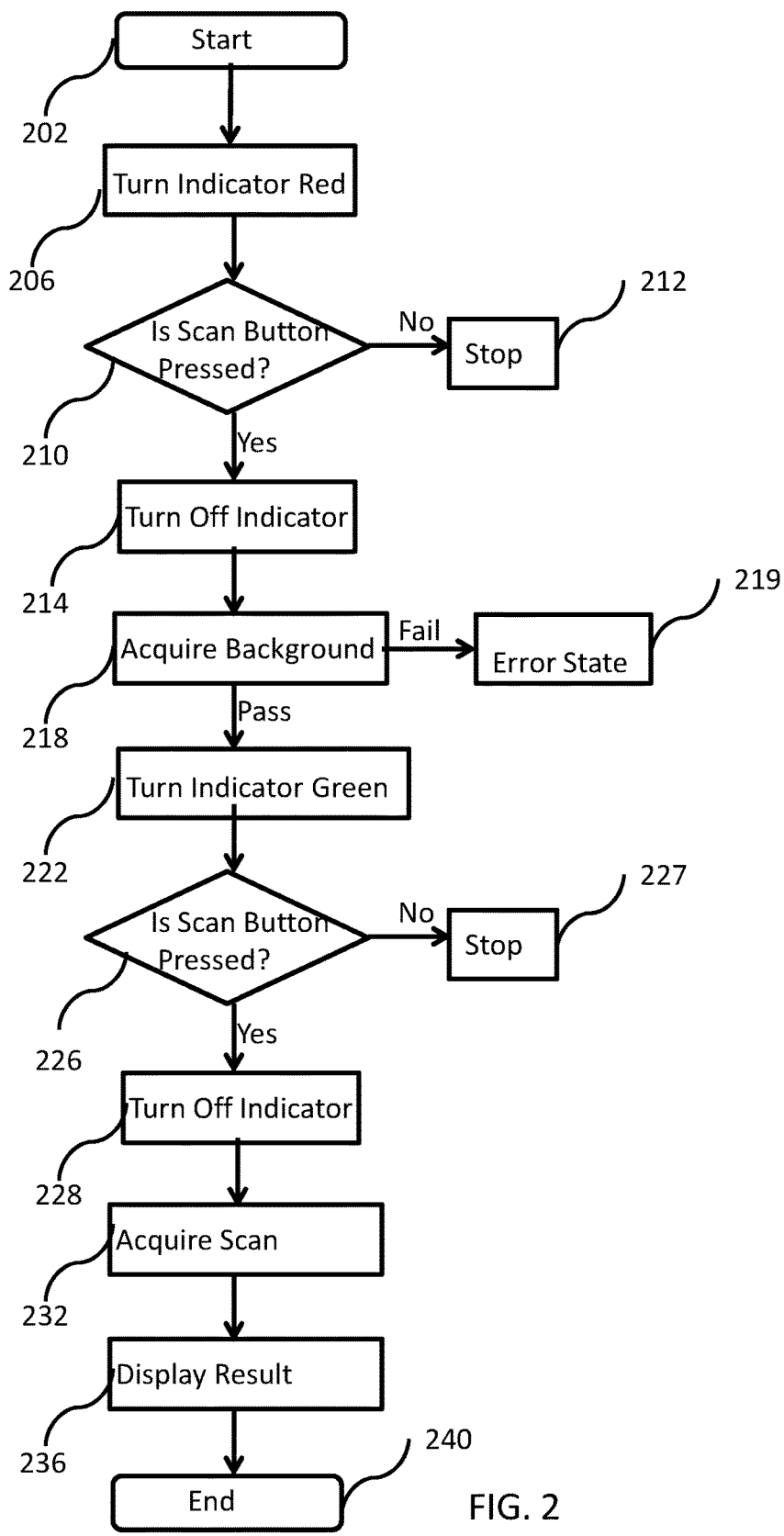
FIG. 2 shows an example flow chart method of the present invention.

In the description of embodiments presented herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

A hand-held spectrometer could contain one or more of the following technologies: Raman, FTIR (mid-IR), NIR (near-IR), laser induced breakdown (LIBS), X-ray fluorescence (XRF) and Quantum cascade laser spectroscopy (QCL).

In infrared (e.g., FTIR) spectroscopy, the unknown substance is illuminated with a broad-spectrum of infrared light, which can be absorbed by the sample of interest. The illumination via a source known to those skilled in the art is often in the wavelength range from about 0.7 microns up to 25 microns. The light intensity as a function of wavelength is measured before and after interacting with the sample, and the absorbance caused by the sample is calculated. Light is absorbed in varying amounts by the sample at particular frequencies corresponding to the vibrational frequencies of the bonds of the molecules in the sample. Since the bonds for every molecule are different, the FTIR absorption spectrum for every molecule is also different. Thus, a spectral "fingerprint" can be generated by recording the absorbance of light as a function of wavelength.

Most substances absorb infrared light very readily, and if all of the light is absorbed, there will be no light reaching the detector to be analyzed. Therefore, care must be taken in how the light is delivered to and collected from the sample. The most user-friendly method for field use is called attenuated total reflection (ATR), and uses an internally reflecting element having a high index of refraction, such as diamond or Germanium, to send light into just the first few microns of the sample before returning back to provide the optical information of the sample.

Many applications exist for portable hand-held spectrometers, including field identification of unknown substances by law enforcement and security personnel in addition to the detection of prohibited substances at airports and in other secure and/or public locations. To be useful in a variety of situations, it is beneficial for a spectrometer to be portable via a handheld form factor instrument that also provides rapid and accurate results.

The measurement instruments and methods disclosed herein thus provide for such a handheld form factor that enables not only ease of transport but also a desired accuracy in results. In particular, the embodiments disclosed herein are configured in compact packages that enable intimate contact between a sample of interest and an ATR optical element positioned in the instrument that enables FTIR investigation of suspected materials. The ATR high index of refraction optical element as configured in the instrument, such as a diamond or Germanium crystal, or a Silicon reflective element, operates by ensuring that non-absorbed incident radiation is directed to a detector after undergoing total internal reflection. As a result, reflected radiation is coupled with high efficiency to the detector, ensuring sensitive operation of the hand-held spectrometer.

Samples of interest can be identified based on the reflected radiation that is measured by the detector. The reflected radiation can be used to derive infrared absorption information corresponding to the sample, and the sample can be identified by comparing the infrared absorption information to reference information for the sample that is stored in the measurement device. In addition to the identity of the sample, the measurement device can provide one or more metrics (e.g., numerical results) that indicate how closely the infrared absorption information matches the reference information. Furthermore, the measurement device can compare the identity of the sample of interest to a list of prohibited substances, also stored within the measurement device, to determine whether particular precautions should be taken in handling the substance, and whether additional actions by security personnel, for example, are warranted.

FTIR spectroscopy typically requires that a background scan be taken before a sample scan. A background scan requires that there is no sample in contact with the sampling interface, which could be ATR, diffuse reflectance, grazing angle or a transmission measurement. In addition to no sample being present, the collection apparatus must be free from sample contamination. A FTIR measurement is obtained in the following order: a background scan is collected, the user is instructed, via the GUI to place the sample onto the collection optic, and data is collected. Once collected, the background is ratioed away from the sample to give a resultant spectrum. This spectrum can be further processed, either onboard or offline to give a sample match state or it may give a quantitative result, identifying how much of a chemical or a mixture of chemicals is present in the sample, by comparison with a spectral library. A sample match state can be one of a positive match state, a mixture match state, a negative match state, or a match error state.

A significant cause of user error when using FTIR spectrometers is originated from any of the following, either individually or in combination:
  a) a user fails to properly clean the collection optic before collecting the background scan;
  b) a user puts the sample onto the collection optics before the background scan, thus preventing analysis.

In order to prevent these user errors, a hand-held spectrometer can have multiple ways in which to direct a user as to how to use FTIR spectrometers. These can be via a graphical user interface (GUI) with use of images, colors and/or words. In addition, the use of lights such as light emitting diodes (LED's) on the spectrometer can indicate to a user when to undertake actions or when not to undertake actions.

Specific Description

As described throughout the present application, the example embodiments herein are beneficially directed to a compact ATR/FTIR optical instrument (i.e., handheld) that overcomes operation in the field when utilized in often cumbersome and visually impaired fashions. A general description of a similar system can also be found in U.S. patent application Ser. No. 13/922,827, entitled: "METHOD AND APPARATUS FOR THE APPLICATION OF FORCE TO A SAMPLE FOR DETECTION USING AN ELECTROMECHANICAL MEANS," to Pastore et al., and assigned to the assignees of the present application, the disclosure of which is hereby incorporated by reference in its entirety. However, where anything in the incorporated reference contradicts anything stated in the present application, the present application prevails.

Turning to the drawings, FIG. 1A and FIG. 1B show isometric cutaway perspectives of an enclosed instrument, generally referenced by the numeral 100, to give the reader a better understanding of the present embodiments. In particular, FIG. 1A shows an example enclosure 156 with elements to be detailed herein of instrument 100, such as, display 136, three visual indicating lights 170, ATR platform 186 and prism surface face 122a (i.e., sensing area). It is to be noted that the dashed lines running from FIG. 1A to FIG. 1B are utilized to enable the reader to appreciate an example indicating lighting 170 configuration of the present invention. It is to also be appreciated that FIG. 1B is utilized to illustrate the hand-held form factor of the instrument 100 and the workings of such an instrument 100 even in a gloved 101 manner.

FIG. 1A also shows a designed non-limiting example anvil arm 191 coupled to an anvil post 194 that can be driven by a desired force mechanism, i.e., actuator (not shown) up (Z as shown in FIG. 1C) for clearance of enclosure 156, angularly moved θ (as shown in FIG. 1C) via an internal gear set (e.g., a motorized internal gear set), and thereafter down for vertical compression of a sample material.

FIG. 1C shows another isometric cutaway of enclosed instrument 100 with the visual indicia, indicating lights 170 and the recessed clearance 198 with the anvil arm 191 raised to a height Z and angularly θ moved to a position over, in particular, surface face 122a so as to be positioned for operation of the instrument, e.g., cleaning and/or measurement of a sample material.

The enclosure 156, as generally noted in FIG. 1A, FIG. 1B and FIG. 1C, is desirably configured with a handheld form factor, so that instrument 100 functions as a handheld infrared spectrometer, and in particular, as a handheld Fourier transform infrared (FTIR) spectrometer. In some embodiments, enclosure 156 can include regions of narrowed width 232 that are positioned and dimensioned to fit the hand of a system operator, so as to facilitate operation of device 100 as a handheld device. In some embodiments, enclosure 156 can also include one or more shock-absorbing external protrusions 230, as generally indicated in FIG. 1A and FIG. 1C. The shock-absorbing external protrusions 230 can be formed (e.g., molded) from a viscoelastic material such as rubber, for example, and are most often configured to reduce or eliminate the transmission of mechanical vibrations to the components within enclosure 156, and generally to protect the components of instrument 100 as well. With respect to dimensional aspects, the embodiments herein are surprisingly even smaller and lighter than previous versions provided by the assignee of the present application, such as the designs disclosed in U.S. Pat. No. 7,928,391, entitled: "Handheld Infrared and Raman Measurement Devices and Methods," to Azimi et al., (hereinafter "Azimi") and assigned to the assignees of the present application, the disclosure of which is hereby incorporated by reference in its entirety. However, where anything in the incorporated reference contradicts anything stated in the present application, the present application prevails. As an example, typical maximum for enclosure 156 is on the order of about 24 cm or less and a width of about 13 cm or less and with a thickness of less than 5 cm. Moreover, the anvil configurations provide for an ergonomic instrument with substantially fewer exposed parts, a provision important for handheld instruments. Overall weight is also correspondingly reduced to less than 1.6 kg based on the compactness of the design.

As noted above, the FTIR workflow, especially when using hand-held instruments, as disclosed herein, has distinct steps when the user must clean the sample area or apply the sample to the sample area. The reader is directed to FIG. 2 to appreciate how a user can initiate operation, to enable such distinct steps, via the use of indicia (i.e., indicator lights 170). However, before turning to the description for FIG. 2, it is to be reiterated that the present invention provides for at least one indicator light 170, often in proximity of the sensing area 122a, such as adjacent to or around the ATR platform 186 to enable an operator to easily and effectively operate the instrument without the operator(s) needing to read the screen. This indicator in the form of a visual light indicator, changes color to indicate the step in the workflow for the user. This is important because if, for example, the user applies a sample to the ATR sensing area 122a during a background scan, the instrument is not able to provide a result. This is the most common user error on all FTIR systems. The light elements behind indicator lighting 170 within instrument 100 may, for example, be light emitting diodes (LED's).

To prevent a user from placing a sample onto the collection optics before or during a background scan, a text instruction can indicate to the user that a scan is progressing and not to place a sample. In addition, a light, or collection of lights, on the top or on the side of the device, close to or next to the collection optics may indicate not to place the sample. The at least one light could be lit in a color highlighting not to take an action, for instance, the at least one light may be red in color. The red color could also indicate that the collection optics are not free of contamination (an example of a background error state, see below). A green color could indicate that no contamination is detected.

Once the background scan has been completed successfully, the light(s) may turn a different color, such as orange or green to highlight that the user can place the sample onto the collection optics. This may be as a sole action or in combination with text instructions and the lights may flash or remain constantly lit. (See FIG. 2).

For users that may have a sight impediment, such as color blindness, the lights may blink in pattern(s) to draw the attention of the user to the current status of the device. Under certain conditions, the lights may change in brightness to more clearly indicate their status.

Thus, turning to the example flow chart method of FIG. 2, an operator in the field pushes a start button 202 and the visual indicator light 170, turns a distinct color to indicate a state of the hand-held spectrometer, and although any color can be chosen for this operation, in the preferred embodiment, the indicator lighting 170 turns red 206. Upon indicator light 170 turning red, the anvil arm 191, if ATR is the operation, is raised to a height Z and angularly θ moved to a position over, in particular, surface face 122a (sensing area) so as to be positioned for operation of the instrument, e.g., cleaning of the screen and the ATR sensing area 122a. The user then presses the scan button activating a scan function of the hand-held spectrometer, and if the embedded software of the instrument 100 recognizes that the scan button has been pressed 210, the software for the instrument turns off 214 the indicator light 170, otherwise the routine ends 212. Instrument 100 then acquires a background measurement 218 and upon completion of the background measurement 218, the indicator light 170 turns a color, preferably green 222, to provide information to the user that the hand-held spectrometer is in a ready-to-scan-sample state, and the user can apply a desired sample to sensing area 122a and thereafter press the scan button (not shown) on the instrument 100 for operation of a measurement. If instrument 100 recognizes that the scan button has been pressed 226, the indicator lighting 170 is turned off 228 and then instrument 100 acquires a scan 232, otherwise the routine ends 227. Results are thereafter displayed 236 and the routine ends 240. If the spectrometer is in an error state following the background measurement 218, then the indicator light 170 changes to an error state 219, which can be at least one of a background error state, a user error state, and an instrument error state, or any combination thereof.

It is to be noted that alternative lighting indicia can also be utilized. For example, the screen 136, as shown in FIG. 1A, can be configured to provide various colors to perform the various tasks, as described above.

Moreover, as to be discussed below, the instrument 100 of the present invention can also provide a Raman workflow. However, while the Raman workflow does not have two phases like FTIR, when there are multiple technologies in a single instrument, the indicator lighting 170 or screen color embodiment, can be used to identify which technology is being used, and when the laser source is active.

As an additional embodiment, multiple colors can be implemented instead of just red and green indicators. For example, multiple colors can be used to indicate when the instrument is waiting for the user to do something, to indicate the type of result (i.e. blue for mixture) or to indicate which technology is selected when two technologies are in one box. Alternatively, different behaviors can also be used to indicate a different status of the instrument. For example, the lights can blink when the instrument is doing an analysis. If three or more lights 170, as shown in FIG. 1A, are provided, then the lights 170 could blink in a clockwise rotating pattern when the instrument is doing an analysis.

In other embodiments, other uses of lights on such a hand-held spectrometer could include:

(a) lights on a hand-held spectrometer, that can include a FTIR, Raman, NIR, LIBS or XRF spectrometer, could indicate, during a measurement scan the signal strength or quality of data;

(b) lights on such a hand-held spectrometer, that can include a Raman spectrometer, may indicate the degree of fluorescence during a measurement scan. Fluorescence may prevent a Raman spectrum from being collected, hinder the identification of the chemical or cause a longer collection time for the sample under measurement;

(c) lights on a hand-held spectrometer could indicate the presence of contamination, thus directing a user to clean the sampling area before proceeding;

(d) lights on a hand-held spectrometer could indicate the result type, once data collection is complete; for example, a green light may indicate a positive match, blue may indicate a mixture result, yellow or orange a similar item and red may indicate that a match was not made from the scan data.

(e) lights on a hand-held spectrometer could indicate if a wireless data transfer is available, a permanently lit light may indicate the function is available and the light may flash when data transfer is actioned.

(f) lights on a hand-held spectrometer could indicate the status of charge of internal batteries, so that when a spectrometer is powered off, but plugged into a charger, a light(s) may indicate the current charge state of the internal battery(s).

(g) the light state, whether flashing or fixed and the flashing pattern, may indicate an error state, on its own or in combination with a message on the screen.

(h) the light state, whether flashing or fixed and the flashing pattern, may indicate the memory is full or close to being filled, on its own or in combination with a message on the screen; and (i) the light state, whether flashing or fixed and the flashing pattern, on its own or in combination with a message on the screen, may indicate a user error with a part of a device, for instance a flex probe may not be inserted correctly, preventing use of the spectrometer.

Figure 3:
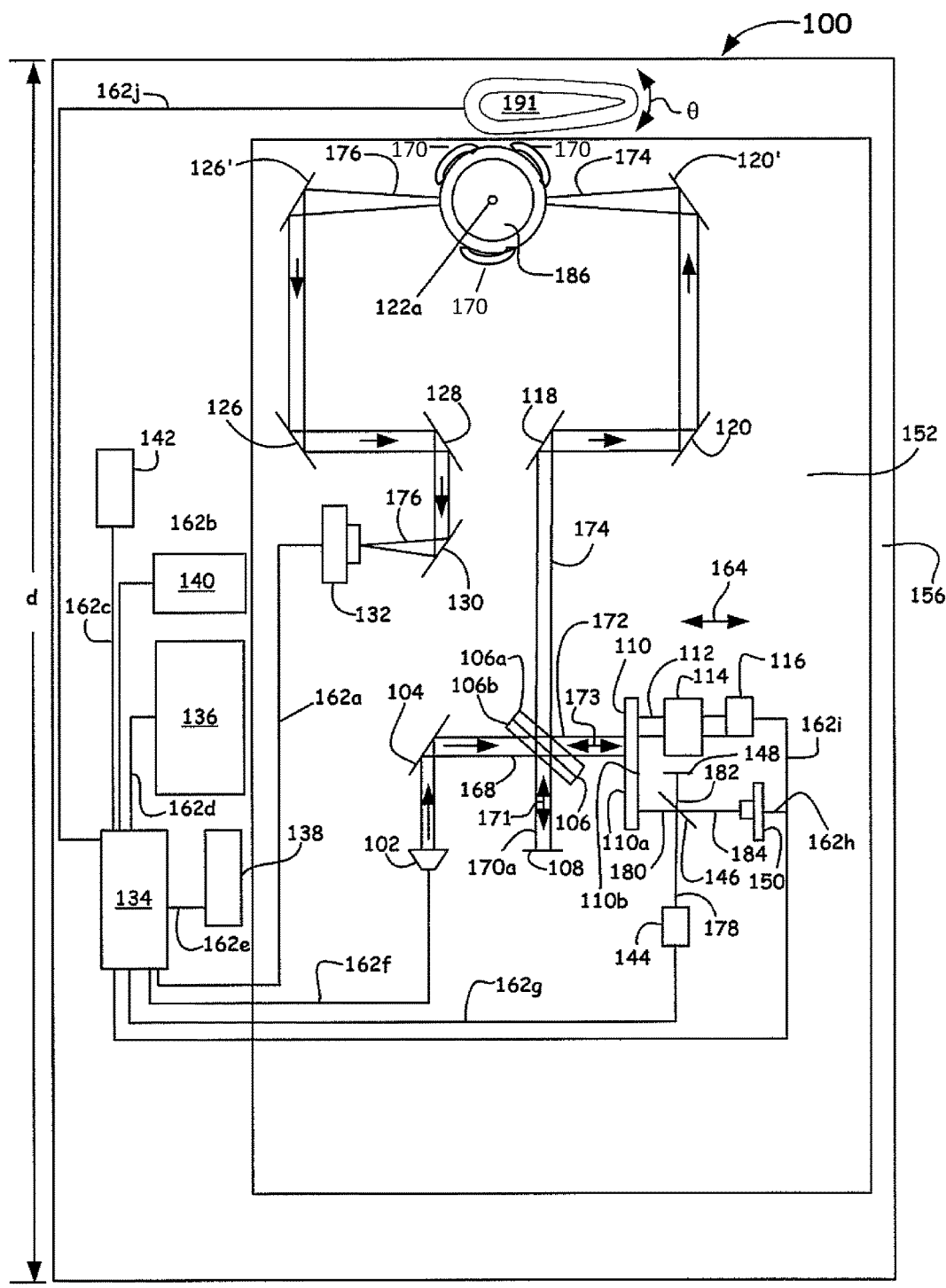
FIG. 3 shows a schematic representation of the workings of an example embodiment.

FIG. 3 is provided to illustrate to the reader the overall workings of an ATR/IR instrument described herein, as a hand-held spectrometer generally referenced by the numeral 100. A similar system can also be found in Azimi.

With respect to the present application, instrument 100 shows assorted optical components mounted on an assembly support 152 within an enclosure 156. Importantly, FIG. 3 also shows an ATR platform 186, three indicator lights 170 around the ATR platform 186, and a movable (rotationally and vertically) sample contact arm (hereinafter anvil arm 191 for simplicity of discussion), i.e., preferably a motorized anvil arm, mounted external to the enclosure 156. It is to be noted that while the instrument shown in FIG. 3 can be externally powered, the complete unit (i.e., instrument 100) can often be powered by a battery for complete portability, preferably by a rechargeable battery, as known to those skilled in the art.

The assorted optical components of FIG. 3 can include: radiation sources 102 and 144; mirrors 104, 108, 110, 148, 118, 120, 120', 126, 126', 128, and 130; beamsplitters 106 and 146; detectors 132 and 150; and an ATR element (e.g., a prism, (not shown)) configured cooperatively with ATR platform 186. It is to be noted that while FIG. 3 shows mirrors 104, 108, 110, 148, 118, 120, 120', 126, 126', 128, and 130 of a certain number and as generally planar in design, it is to be noted that other optical elements of any number, to include refractive optical elements (e.g., lenses) as well as non-planar reflective elements can also be configured with other predetermined curvatures to provide the optical paths shown in FIG. 3. For example, such elements can be configured with concave, convex, parabolic, or elliptical curvatures or any general surface needed to provide proper beam construction along any part of the beam paths as directed within instrument 100.

As shown in FIG. 3, instrument 100 also includes a shaft 112, a bushing 114, and an actuator 116 coupled to mirror 110, and an electronic processor 134, an electronic display 136 (e.g., including a flat panel display element such as a liquid crystal display element, an organic light-emitting diode display element, an electrophoretic display element, or another type of display element), an input device 138, a storage unit 140, and a communication interface 142. Also shown in FIG. 3 is an electronic processor 134 that is in electrical communication with detector 132, storage unit 140, communication interface 142, display 136, input device 138, radiation sources 102 and 144, detector 150, movable anvil arm 191, and actuator 116, respectively, via communication lines 162a-j. The processor 134 is also configured to control the at least one indicator light 170 (shown in FIGS. 1A-1C) to indicate a state of the hand-held spectrometer 100.

Instrument 100, if configured for use as a Fourier transform infrared (FTIR) spectrometer during operation, provides radiation 168 via radiation source 102, which can be removable for ease of replacement, under the control of processor 134. Radiation 168 is directed by mirror 104 to be incident on beamsplitter 106, configured as a beamsplitting optical element 106a and a phase compensating plate 106b to enable the received radiation 168 to be divided into two beams. Using such a configuration enables a Michelson-type of interferometer to be formed wherein a first beam 170a reflects from a surface of beamsplitter 106, propagates along a beam path which is parallel to arrow 171, and is incident on fixed mirror 108. Fixed mirror 108 thereafter reflects first beam 170a in an opposite direction so as to now be directed towards beamsplitter 106. A second beam 172 is transmitted through beamsplitter 106 and propagates along a beam path which is parallel to double arrow 173. Second beam 172 is incident on a first surface 110a of movable mirror 110 so that upon reflection is also directed towards beamsplitter 106.

First and second beams 170a and 172 are thus combined by the configuration of beamsplitter 106 and associated optics, which spatially overlaps the beams to form a beam of modulated infrared radiation beam 174 (by way of operation of the configured Michelson interferometer) and is directed towards mirror 118. Thereafter, mirrors 118, 120, 120' direct modulated infrared radiation beam 174 to an ATR optical element (not shown in detail but ATR surface face 122a is illustrated). Once inside the ATR optical element (often configured as a prism), beam of modulated infrared light 174 is directed to a surface face 122a (shown as a plan view in FIG. 3) of the ATR optical element (e.g., a prism). Surface face 122a of the ATR optical element is positioned such that it contacts a sample of interest (not shown), often a sample having irregularities in surface construction (e.g., a powder). When modulated infrared light 174 is incident on surface face 122a, a portion of the radiation of modulated infrared light 174 is coupled into the sample material (not shown) through surface 122a via a desired evanescent wave effect, as known to those of ordinary skill in the art. As part of the effect, the sample desirably absorbs a portion of modulated infrared light 174 that is indicative of the structure and thus the properties of the sample material.

The total internal reflected portion of modulated infrared light 174, denoted as reflected beam 176, now includes a reduced amount of modulated radiation not absorbed by the sample (not shown), of which is also indicative of the properties of the sample (not shown). As a result of the configuration, reflected beam 176 is directed through a desired surface of the ATR optical element and is thereafter directed by, for example, mirrors 126', 126, 128, and 130 in order to be interrogated by instrument 100 via detection by detector 132. In particular, under the control of processor 134, detector 132 can be configured to measure one or more properties of a sample (not shown) based on the reflected radiation in beam 176.

As stated above, the configured mirrors 108 and 110 together with beamsplitter 106 beneficially form a Michelson interferometer. In operation, by translating mirror 110 as indicated by double-arrow 164 prior to each measurement, the plurality of measurements of the radiation in reflected beam 176 form an interferogram that includes information, such as sample absorption information. Processor 134 can be configured to apply one or more mathematical transformations (e.g., a Fourier transform) to the interferogram to obtain the sample absorption information. For example, processor 134 can be configured to transform the interferogram measurements from a first domain (such as time or a spatial dimension) to a second domain (such as frequency) that is conjugate to the first domain.

To provide movement of mirror 110, the element itself is coupled to shaft 112, bushing 114, and actuator 116. The shaft 112 moves freely within bushing 114 and a viscous fluid is often disposed between shaft 112 and bushing 114 to permit relative motion between the two. Thus, mirror 110 moves when actuator 116 receives control signals from processor 134 via communication line 162i. Actuator 116 initiates movement of shaft 112 in a direction parallel to arrow 164 and mirror 110 moves in concert with shaft 112. Bushing 114 provides support for shaft 112, preventing wobble of shaft 112 during translation. However, bushing 114 and shaft 112 are effectively mechanically decoupled from one another by the fluid disposed between them; and thus mechanical disturbances, such as vibrations, are coupled poorly between shaft 112 and bushing 114. As a result, the alignment of the resultant Michelson interferometer remains relatively undisturbed even when mechanical perturbations, such as vibrations, are present in other portions of instrument 100.

To measure the position of mirror 110, instrument 100 provides an assembly that includes radiation source 144, beamsplitter 146, mirror 148, and detector 150. These components are arranged to form a second Michelson interferometer. During a mirror position measurement of operation, radiation source 144 (e.g., a monochromatic emission source (laser)) receives a control signal from processor 134 via communication line 162g, and generates a radiation beam 178. As an example of a desired source, radiation source 144 can be a configured vertical cavity surface-emitting laser (VCSEL) that generates radiation having a central wavelength of 850 nm. However, it is to be understood that source 144 can also include a wide variety of other sources, such as, laser diodes, light-emitting diodes, etc., capable of having radiation between 400 nm up to about 1200 nm.

Turning back to the discussion for FIG. 3, beam 178 is incident on beamsplitter 146, which separates radiation beam 178 into a first beam 180 and a second beam 182. First beam 180 reflects from the surface of beamsplitter 146 and is incident on a second surface 110b of mirror 110. Second surface 110b is positioned opposite first surface 110a of mirror 110. First beam 180 reflects from surface 110b and returns to beamsplitter 146.

Second beam 182 is transmitted through beamsplitter 146, reflected by mirror 148, and returned to beamsplitter 146. Beamsplitter 146 combines (e.g., spatially overlaps) reflected beams 180 and 182, and the spatially overlapped beam 184 is directed to detector 150. Detector 150 receives control signals from processor 134 via communication line 162h, and is configured to measure an intensity of combined beam 184. Combination beam 184 provides an interference pattern that contains desired optical position information. Thus, monitoring beam 184 enables the position (and speed and tilt, if desired), of mirror 110 to be precisely determined by counting the peaks and valleys in the amplitude of beam 184.

As a beneficial aspect of the present application, absorption information can be compared by processor 134 to reference information (e.g., reference absorption information) stored in storage unit 140 to determine an identity of an unknown sample (not shown). For example, processor 134, after a Fourier transform has been applied to the received reflected beam 176, can determine whether the absorption information for the sample matches any one or more of a plurality of sets of reference absorption information for a variety of substances that are stored as database records in storage unit 140 or even from a database remotely located via wireless communication. If a match is found (e.g., the sample absorption information and the reference information for a particular substance agree sufficiently), then sample 190 is considered to be identified by processor 134. Processor 134 can send an electronic signal to display 136 along communication line 162d that indicates to a system operator that identification of sample 190 was successful, and provides the name of the identified substance. The signal can also indicate to the system operator how closely the sample absorption information and the reference information agree. For example, numeric values of one or more metrics can be provided which indicate the extent of correspondence between the sample absorption information and the reference information on a numerical scale.

If a match between the sample absorption information and the reference information is not found by processor 134, the processor can send an electronic signal to display 136 that indicates to the system operator that sample 190 was not successfully identified, or that efficient optical coupling between the ATR surface face 122a was not provided because of insufficient force applied by movable anvil arm 191. The electronic signal can include, in some embodiments, a prompt to the system operator to repeat the sample absorption measurements or perhaps choose an operation that can provide ample anvil arm 191 contact force.

If identification of sample 190 is successful, processor 134 can be configured to compare the identity of sample 190 against one or more lists of prohibited substances stored in storage unit 140. If sample 190 appears on a list as a prohibited substance, processor 134 can alert the system operator that a prohibited substance has been detected. The alert can include a warning message provided on display 136 and/or a colored region (e.g., a red-colored region) on display 136. Processor 134 can also be configured to sound an audio alarm via a speaker to alert the system operator.

Instrument 100 also includes communication interface 142, which receives and transmits signals from/to processor 134 via communication line 162c. Communication interface 142 includes a wireless transmitter/receiver unit that is configured to transmit signals from processor 134 to other devices, and to receive signals from other devices and communicate the received signals to processor 134. Typically, for example, communication interface 142 permits processor 134 to communicate with other devices via a wireless network that includes multiple devices connected to the network, and/or via a direct connection to another device. Processor 134 can establish a secure connection (e.g., an encrypted connection) to one or more devices to ensure that signals can only be transmitted and received by devices that are approved for use on the network.

Processor 134 communicates with a central computer system to update the database of reference information stored in storage unit 140. Processor 134 is configured to periodically contact the central computer system to receive updated reference information, and processor 134 can also receive automatic updates that are delivered by the central computer system. The updated reference information can include reference absorption information, for example, and can also include one or more new or updated lists of prohibited substances.

Processor 134 can also communicate with other measurement devices to broadcast alert messages when certain substances, such as substances that appear on a list of prohibited substances, are identified, for example. Alert messages can also be broadcast to one or more central computer systems. Alert information, including the identity of the substance, the location at which the substance was identified, the quantity of the substance, and other information, can also be recorded and broadcast to other measurement devices and computer systems.

In some embodiments, instrument 100 can be connected to other devices over other types of networks, including isolated local area networks and/or cellular telephone networks. The connection can also be a wireless connection or a physical coupling.

As non-limiting examples of a wireless connection, such an arrangement can include commercial wireless interfaces, such as but not limited to, radio waves (WiFi), infrared (IrDA), or microwave technologies that also allow integration into available portable personal devices, such as, but not limited to, cell phones, pagers, personal identification cards, laptops, etc. The wireless communication can thus provide signals, including alert messages if detected, to be transmitted from processor 134 to such network-enabled devices that can alert personnel in the event that particular suspects are detected by instrument 100.

The wireless network can, for example, optionally include an open standard for short-range transmission of digital voice and data between the aforementioned portable but also fixed devices that support point-to-point and multipoint applications. For example, communication interface 142, as shown in FIG. 3, can be configured with Bluetooth, which operates in a globally available frequency band (i.e., 2.4 GHz), ensuring communication compatibility worldwide, or Electronic and Electrical Engineers IEEE technologies (e.g., (IEEE) 802.11a or IEEE 802.11b) as the communication means based on its present common use in both business and home environments. Such popular technologies enable users' high-speed access to networks and the Internet while roaming throughout an area. Moreover, other protocols for wireless, such as IEEE 802.15, IEEE 802.16, GPS, 3G, 4G, and others, may also be configured as a protocol for the communication standard of the present embodiments disclosed herein.

With respect to physical wired coupling, the coupling can be by way of a dedicated coupling I/O means, such as a USB port (not shown) to provide, for example, operational data (feedback) via the embedded software (e.g., firmware) or instructions received from processor 134 for programmatic control instruction.

Typically, the desired input device 138 includes a control panel that enables a system operator to set configuration options and change operating parameters of instrument 100. In some embodiments, instrument 100 can also include an internet-based configuration interface that enables remote adjustment of configuration options and operating parameters. The interface can be accessible via a web browser, for example, over a secured or insecure network connection. The internet-based configuration interface permits remote updating of instrument 100 by a central computer system or another device, ensuring that all measurement devices that are operated in a particular location or for a particular purpose have similar configurations. The internet-based interface can also enable reporting of device configurations to a central computer system, for example, and can enable tracking of the location of one or more measurement devices.

Turning to the radiation source for the instrument 100, radiation source 102, which is often configured as a replaceable component, includes a broadband radiation source configured to provide infrared radiation so that instrument 100 can be operated as an infrared spectrometer. Typically, for example, the infrared radiation provided by source 102 includes a distribution of wavelengths, with a center wavelength of the distribution of about 10 microns. In general, radiation source 102 can include a variety of sources known to those skilled in the art, including a heated infrared source chosen from any customized or conventional known source utilized in the field, such as, but not limited to, a wire, metal or ceramic element that is heated to emit a continuous band of optical radiation.

Typically, a characteristic temperature of the quasi-blackbody distribution of wavelengths of the radiation provided by source 102 can be between 700° C. up to 2000° C. and with emissivity between 0.4 and 0.95. It is to be noted, however, that the temperature of radiation 168 can be varied (e.g., via a control signal from processor 134 transmitted along communication line 162*f*) according to the particular sample 190 and the sensitivity of detector 132. Suitable broadband detectors 132 to generate an electronic signal include a pyroelectric detector or other detection elements, such as, bolometers, lead salt detectors, mercury cadmium telluride detectors, a photodiode, avalanche photodiode, linear or 2D array or any detection element that can generate an electronic signal when subjected to an intensity of either beam 176 or beam 184. Photodiodes, avalanche photodiodes, quadrant photodiodes, or 2D arrays are desirable with respect to detector 150, with the multi-element detectors being used with dynamic alignment.

ATR/Prism Assembly Discussion

Figure 4:
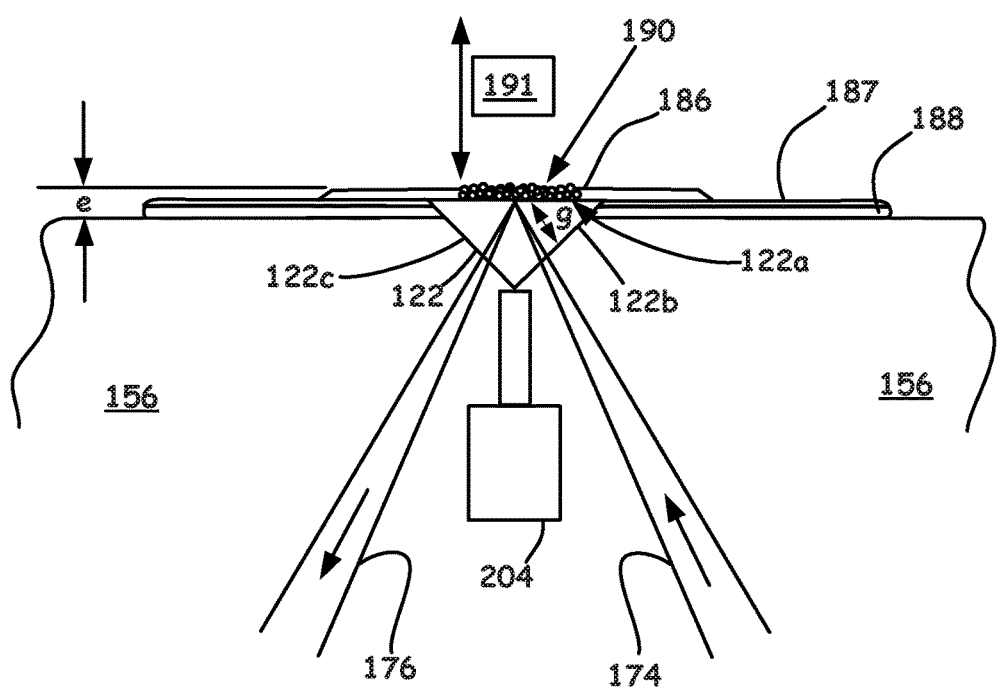
FIG. 4 shows an example diagram of a sample platform and ATR assembly.

FIG. 4 shows an enlarged general view of the ATR platform 186, 187, etc., and reflective element (hereinafter prism 122). Prism 122 includes a surface 122*a* positioned to contact sample 190 (e.g., shown as a powder (denoted as circles)), which can be a solid or a liquid desired to be measured using ATR principles. Radiation from a source 102 configured within instrument 100, as described above and shown in FIG. 3, enters prism 122 through surface 122*b*, and leaves prism 122 through surface 122*c*.

An edge of prism 122 opposite to surface 122*a* is also but not necessarily supported from below by a prism base 204. A coating (not shown), such as a metal (e.g., gold), is also often applied to prism 122 to enable stable coupling to the top of configured surface 156 of instrument 100 to also provide support to prism 122 from above. Support provided by surface 156 and base 204 allows prism 122 to withstand significant applied forces during operation without being displaced from its mounting position.

As a general principle of operation of the instrument, after a solid unknown material 190 to be examined is placed on the attenuated total reflectance (ATR) element, i.e., surface face 122*a*, as also shown in FIG. 3, a sample contact actuator (e.g., an anvil actuator, not shown) applies a desired contact force to the sample material against the ATR surface face 122*a*. The actuator can, for example, be a motor (e.g., a DC motor) or a solenoid, an electromagnetic solenoid, or any type of force actuator (e.g., piezo-electric driven mechanism, linear motors, pneumatic or hydraulic actuators, etc.) that can be moved in a controlled manner to provide known or desired controlled compressive forces. Such actuators can also include cam or scissor jack configurations and if configured as a solenoid, such a solenoid can be, for example, a rotary solenoid that drives a pressure mechanism. The applied contact force using such actuators, while possibly being a fixed force or even a user-selectable force, more often can be automatically controlled through feedback, as previously discussed, from the spectrometer based on the spectrometer signature of the sample.

During operation, a system operator can motor control vertical movement of anvil arm 191. Angular position θ of anvil arm 191, while capable of also being motor driven is more often manually provided by the user prior to operation of the instrument 100 for measurement(s). Thus, upon the sample being disposed on platform 186, and the sample contact arm (e.g., anvil arm 191) thereafter raised and rotated into position, a known or controlled compressive force of the sample material with prism 122 (e.g., surface face 122a) is provided automatically by the anvil actuator (not shown). Such a manipulation provides intimate contact between surface face 122a and sample material 190 to enable efficient coupling of the evanescent wave and improve a signal-to-noise ratio in measurements of reflected radiation beam 176. Support base 204 and surface 156 ensure that prism 122 remains in the same position within enclosure 156 during operation.

It is to be noted that ATR platform 186 extends outward for a distance e from surface 156. Generally, e can be between about 3 mm up to about 5 mm in height. Platform 186 permits contact between sample 190 and surface 122a of prism 122 via a preferable planar surface configuration that results in an opening (not shown in detail) in platform 186 to surface face 122a. However, it is to be noted that while a planar surface configuration for platform 186 is preferred, other surfaces, e.g., curved concave surfaces, can also be implemented to enable receiving materials for ATR optical investigation, as configured with other aspects of the present application. An integral part of platform 186 is an extended section 187 that is configured with a moat-like configuration designed with a curvature so as to catch any material that spills over from platform 186. A liquid-proof and often hermetic seal 188 is coupled to the platform (186 and 187) and surface. It is to be noted that prism 122 is mechanically coupled to the optical engine 152 but isolated from the housing 156 of instrument 100 to prevent the transmission of large-amplitude mechanical perturbations.

It is noted that the present invention can provide FTIR absorption information to identify a sample. In some embodiments, sample information in addition to infrared absorption information can also be used to identify the sample. For example, instrument 100 can be configured to cooperate with other scanning systems to identify samples of interest. Suitable other scanning systems can include, for example, handheld and non-handheld Raman scanning systems. To identify a sample, the sample can first be scanned with a Raman scanning system that is configured to determine an identity of the sample based on Raman scattering information about the sample. The identity determined by the Raman scanning system is then transmitted to instrument 100 and received via communication interface 142, as shown in FIG. 1.

Instrument 100 can also be configured as a single handheld device to also separately determine an identity of the sample based on Raman scattering, as similarly disclosed in U.S. Pat. No. 7,928,391, the disclosure of which is hereby incorporated by reference in its entirety. However, where anything in the incorporated reference contradicts anything stated in the present application, the present application prevails. Thus, if the identities determined via FTIR information and Raman scattering information agree, instrument 100 can also report a successful identification to a system operator. If the identities do not agree, measurement device 100 can report a failed identification. More generally, both the Raman scanning system and instrument 100 can be configured to determine an identity of the sample, and a numerical score or metric that is related to an extent of correspondence between the measured sample information and reference information for the sample. Instrument 100 can then determine, based on the identities reported and the values of the metrics, whether the identification process was successful or not, and to what extent the reported identity of the sample is trustworthy.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Such modifications and the like are considered simple modifications that are well within the ability of one of ordinary skill in the art and within the scope and spirit of the invention. Accordingly, many such modifications may be made by one of ordinary skill in the art without departing from the spirit, scope and essence of the invention. Neither the description, drawings nor the terminology is intended to limit the scope of the invention—the invention is defined by the claims.

We claim:

1. A method for providing a visual indicator of a workflow, comprising:
    performing a background data collection operation in the absence of a sample on a sensing area positioned on a top side of an FTIR instrument, wherein one or more indicator lights arranged on the top side of the FTIR instrument in a ring formation around the sensing area turns to a first color that indicates to a user when the background data collection operation has completed, and the user has obscured visibility that limits the ability to read information on a screen;
    applying the sample to a surface of the sensing area surrounded by the one or more indicator lights if the first color does not indicate an error state;
    measuring a spectrum of the sample;
    processing the spectrum and background data to determine a sample match state to a known material, wherein the one or more indicator lights turn to a second color that indicates the sample match state to the user.

2. The method of claim 1, wherein:
    prior to performing the background data collection operation, initiating the FTIR instrument for operation wherein the one or more indicator lights turn to a color that indicates to the user that no sample should be applied to the sensing area.

3. The method of claim 2, wherein:
    the step of initiating includes cleaning the sensing area.

4. The method of claim 1, wherein:
    the sample match state comprises a positive match state, a mixture match state, a negative match state, and a error match state.

5. The method of claim 1, wherein:
    the first or second color provided by the one or more indicator lights comprise a level of brightness.

6. The method of claim 1, wherein:
    the first or second color provided by the one or more indicator lights comprise blinking in a pattern.

7. The method of claim 6, wherein:
the blinking in a pattern comprises a clockwise rotating pattern of a plurality of the indicator lights.

8. The method of claim 1, wherein:
the known material comprises an explosive, a narcotic, a biological, or a toxic material.

9. The method of claim 1, wherein:
the one or more indicator lights turn to a color that indicates a signal strength state.

10. The method of claim 1, wherein:
the first color that indicates the background data collection operation has completed comprises a ready-to-scan-sample state or the error state.

11. A system that provides a visual indicator of a workflow, comprising:
a portable hand-held an FTIR instrument comprising:
a sensing area positioned on a top side of the FTIR instrument;
one or more indicator lights arranged on the top side of the FTIR instrument in a ring formation around the sensing area;
a radiation source configured to direct radiation at a sample disposed on a surface of the sensing area;
a processor configured to analyze a spectrum and background data detected by the sensing area in response to the radiation and control the plurality of lights;
wherein the one or more indicator lights in the ring formation around the sensing area turns to a color that indicates to a user that has obscured visibility that limits the ability to read information on a screen of 1) completion of a background data collection operation in the absence of a sample on the sensing area, wherein the sample is applied to the surface of the sensing area if a first color for the background data collection operation provided by the one or more indicator lights does not include an error state; and 2) a second color that indicates a sample match state to a known material determined from the spectrum and background data.

12. The system of claim 11, wherein:
the sample match state comprises a positive match state, a mixture match state, a negative match state, and a error match state.

13. The system of claim 11, wherein:
the first or second color provided by the one or more indicator lights comprise a level of brightness.

14. The system of claim 11, wherein:
the first or second color provided by the one or more indicator lights comprise blinking in a pattern.

15. The system of claim 14, wherein:
the blinking in a pattern comprises a clockwise rotating pattern of a plurality of the indicator lights.

16. The system of claim 11, wherein:
the known material comprises an explosive, a narcotic, a biological, or a toxic material.

17. The system of claim 11, wherein:
the one or more indicator lights turn to a color that indicates a signal strength state.

18. The system of claim 11, wherein:
the first color that indicates the background data collection operation has completed comprises a ready-to-scan-sample state or the error state.

\* \* \* \* \*